United States Patent [19]

Summerton et al.

[11] 4,123,610

[45] Oct. 31, 1978

[54] NUCLEIC ACID CROSSLINKING AGENT AND AFFINITY INACTIVATION OF NUCLEIC ACIDS THEREWITH

[75] Inventors: James E. Summerton, Denver, Colo.; Paul A. Bartlett, El Carrito, Calif.

[73] Assignee: The United States Government, Washington, D.C.

[21] Appl. No.: 775,800

[22] Filed: Mar. 9, 1977

[51] Int. Cl.$^2$ ............... C07H 19/20; C07H 19/10; C07H 21/02
[52] U.S. Cl. .......................... 536/28; 424/180; 260/561 H; 536/22; 536/29
[58] Field of Search ................ 536/22, 28, 29; 260/561 H

[56] References Cited

U.S. PATENT DOCUMENTS

| 2,355,911 | 8/1944 | Graenacher et al. | 536/22 |
| 3,133,912 | 5/1964 | Kimmig et al. | 536/22 |
| 4,018,916 | 4/1977 | VereHodge | 536/29 |
| 4,021,542 | 5/1977 | Schmidt et al. | 536/22 |

*Primary Examiner*—Johnnie R. Brown
*Attorney, Agent, or Firm*—Holman & Stern

[57] ABSTRACT

The crosslinking agent contains an acylhydrazide moiety, through which it is linked to a cytosine residue on the first chain; and an α-haloketal moiety which, after attachment of the crosslinking agent to the first chain, is hydrolyzed to an α-haloketone moiety, through which linking is effected to the base-paired guanine residue on the second chain.

12 Claims, No Drawings

NUCLEIC ACID CROSSLINKING AGENT AND AFFINITY INACTIVATION OF NUCLEIC ACIDS THEREWITH

BACKGROUND OF THE INVENTION

This invention relates to nucleic acids and, more particularly, to novel nucleic acid crosslinking agents and the use of such crosslinking agents in the affinity inactivation of nucleic acids.

All living organisms contain nucleic acids in the form of deoxyribonucleic acid (DNA) and ribonucleic acid (RNA). These nucleic acids, which consist of polynucleotide chains of varying nucleotide sequences, contain the information which directs all forms of life on our planet. It is generally accepted that during information transfer processes within cells, i.e., during replication (DNA synthesis), transcription (RNA synthesis), and translation (protein synthesis), nucleic acids exist in two different transient states, i.e., in a single-stranded configuration and in a double-helical configuration wherein two chains or strands of complementary nucleotide sequence are based-paired to each other. During the information transfer processes, the base-paired chains readily dissociate from each other into the single-stranded configuration, and each chain then serves as a template for the synthesis of two complementary chains, each newly synthesized chain then becoming base-paired to its complementary template chain.

Since the information transfer processes rely upon the ability of the base-paired chains to readily dissociate into the single-stranded configuration, the formation of interstrand crosslinks between the base-paired chains which prevent such dissociation from occurring renders the nucleic acids incapable of being replicated, transcribed or translated, and hence biologically dead. A number of bifunctional chemical compounds are known which are capable of crosslinking certain nucleic acids in this manner. Several of these nucleic acid crosslinking agents have been utilized in simple in vitro systems for the purposes of selectively crosslinking and inactivating a specific nucleotide sequence by means of affinity techniques. In such affinity inactivation procedures, the crosslinking agent is first attached through one of its functional moieties to a single-stranded oligonucleotide carrier chain. When this derivatized oligonucleotide carrier chain is contacted with a single-stranded oligonucleotide target chain having a nucleotide sequence complementary to that of the carrier chain, the target chain becomes base-paired to the carrier chain and then reacts with the free functional moiety of the crosslinking agent to thereby crosslink the two chains.

The nucleic acid crosslinking agents which have previously been proposed for use in affinity inactivation procedures, all have certain limitations which restrict their application to only certain types of nucleic acids and in only very simple in vitro systems. The major difficulty with all of these crosslinking agents lies in the particular reactive sites which they require on the polynucleotide carrier chain for successful attachment thereto. These particular attachment sites are either totally lacking in a vast number of nucleic acids or, if present, are such that they enable only one molecule of crosslinking agent to be attached per polynucleotide chain. This limitation precludes their use in complex in vitro systems or in vivo wherein it is desired to irreversibly inactivate a relatively long nucleotide sequence, since a single interstrand crosslink in such cases would not be likely to be sufficiently stable to effect irreversible inactivation due to depurination reactions and the ability of cells to repair low levels of interstrand crosslinks.

In attempting to overcome the above-described limitations and develop nucleic acid crosslinking agents having greater versatility in complex systems than those previously proposed, a number of important factors must be taken into consideration involving the proper selection, coordination and spacing of the attaching moiety (i.e., the functional group of the crosslinking agent which links to the attachment site of the polynucleotide carrier chain) and the crosslinking moiety (i.e., the functional group of the crosslinking agent which reacts at the crosslinking site of the polynucleotide target chain). First of all, the attaching moiety must be such that it will be reactive with one or more residues or groups common to a vast majority of nucleic acids and generally present therein in sufficient number so as to enable multiple attachment sites on the carrier chain. Secondly, the crosslinking moiety must be such that it will be unreactive with the carrier chain during attachment of the crosslinking agent to the carrier chain and hence will not form intrastrand crosslinks, but will be reactive with the target chain upon base-pairing of the two chains so as to form interstrand crosslinks. Thirdly, the attaching moiety and the crosslinking moiety must be properly coordinated and spaced with respect to each other that upon base-pairing of the derivatized carrier chain to the target chain, the crosslinking moiety of each attached molecule of crosslinking agent will be properly positioned with respect to a reactive crosslinking site on the target chain so that it may react therewith. In addition to these basic requirements, the crosslinking moiety should have sufficient stability and reaction specificity in biological systems so as to be capable of withstanding premature deactivation before the derivatized carrier chain has been able to become base-paired with its target chain. None of the previously proposed nucleic acid crosslinking agents has been able to satisfy all of the foregoing requirements.

SUMMARY OF THE INVENTION

It is accordingly a primary object of the present invention to provide a novel crosslinking agent for nucleic acids which is capable of forming interstrand crosslinks between the base-paired complementary polynucleotide chains of double-stranded nucleic acids, and which has greater versatility with respect to a wide range of nucleic acids than the crosslinking agents previously proposed for this purpose.

Another object of the invention is to provide a nucleic acid crosslinking agent in accordance with the preceding objects, which may be utilized in affinity inactivation procedures for selectively inactivating any of a vast number of nucleic acids of varying types, nucleotide sequences and polynucleotide chain lengths.

A further object of the invention is to provide a nucleic acid crosslinking agent in accordance with the preceding objects, which has an attaching moiety which enables it to be attached to any of a vast number of single-stranded polynucleotide carrier chains of varying types and nucleotide sequences.

Still another object of the invention is to provide a nucleic acid crosslinking agent in accordance with the preceding object, which has an attaching moiety enabling its attachment to such polynucleotide carrier chains at multiple attachment sites on the carrier chain.

Still a further object of the present invention is to provide a nucleic acid crosslinking agent in accordance with the preceding objects, which has a crosslinking moiety which is unreactive with the polynucleotide carrier chain under the conditions of attachment of the crosslinking agent to the carrier chain, but which may be subsequently activated under conditions non-detrimental to the derivatized carrier chain so as to render it reactive with a polynucleotide target chain whose nucleotide sequence is complementary to that of the carrier chain.

Another object of the invention is to provide a nucleic acid crosslinking agent in accordance with the proceding objects, whose attaching moiety and crosslinking moiety are properly coordinated and spaced with respect to each other so that upon base-pairing of the derivatized carrier chain to its complementary target chain, the crosslinking moiety of each molecule of attached crosslinking agent will be in proper position with respect to a reactive crosslinking site on the target chain so as to be able to react therewith.

A further object of the invention is to provide a nucleic acid crosslinking agent in accordance with the preceding objects, whose crosslinking moiety when activated has sufficient stability and reaction specificity in biological systems so as to be capable of withstanding premature deactivation before the derivatized carrier chain has been able to become base-paired to its complementary target chain.

Yet another object of the invention is to provide an affinity nucleic acid-inactivating agent utilizing the nucleic acid crosslinking agent in accordance with the preceding objects, and which is capable of selectively inactivating a guanine residue-containing single-stranded polynucleotide target chain having a designated nucleotide sequence by base-pairing and covalently crosslinking therewith.

A yet further object of the invention is to provide a method utilizing the nucleic acid crosslinking agent in accordance with the preceding objects for the selective inactivation of a guanine residue-containing single-stranded polynucleotide target chain having a designated nucleotide sequence.

The above and other objects are achieved in accordance with the present invention by providing a nucleic acid cross-linking agent consisting of a bifunctional compound having a cytosine residue-reactive acylhydrazide moiety separated by a chain of methylene groups from a α-haloketal moiety which is hydrolyzable to a guanine residue-reactive α-haloketone moiety. The crosslinking agent of the present invention has the formula

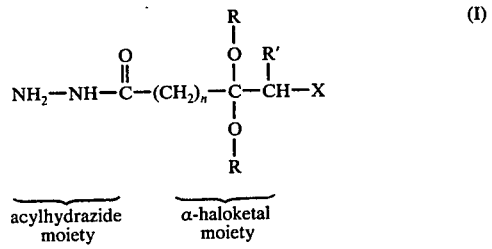

acylhydrazide moiety    α-haloketal moiety wherein $n$ is an integer of from 2 to 4; $R'$ is hydrogen or methyl; $X$ is Cl or Br; and, $R$ is methyl or ethyl.

The nucleic acid crosslinking agent of the present invention may be utilized in affinity inactivation procedures for selectively inactivating any guanine residue-containing single-stranded polynucleotide target chain having a designated nucleotide sequence. When so utilized, the acylhydrazide moiety is the attaching moiety of the crosslinking agent, and the α-haloketal moiety is the crosslinking moiety thereof in its unreactive protected form. The crosslinking agent is first covalently linked through its acylhydrazide moiety to the cytosine residues of a single-stranded polynucleotide carrier chain which has a nucleotide sequence complementary to the designated nucleotide sequence of the target chain. Under the conditions required for this attachment step, the α-haloketal moiety of the crosslinking agent remains stable and will not react with the carrier chain. Following the attachment step, the derivatized carrier chain is activated by hydrolyzing the α-haloketal moiety of the attached crosslinking agent to the guanine residue-reactive α-haloketone moiety

wherein $R'$ and $X$ have the meanings defined above), which is the deprotected reactive form of the cross-linking moiety of the crosslinking agent. When the activated derivatized carrier chain is then contacted with the target chain, the two complementary polynucleotide chains become base-paired. The resulting base-paired configuration brings the α-haloketone moiety of the activated derivatized carrier chain into proper position with respect to a guanine residue of the target chain so that it may react therewith to covalently crosslink the two chains and thereby inactivate the target chain.

The cytosine residue-reactivity of the attaching moiety of the crosslinking agent of the present invention provides it with a high degree of versatility not possessed by any of the previously proposed nucleic acid crosslinking agents. This is so due to the fact that virtually all naturally occurring nucleic acids, including both DNA and RNA nucleic acids, contain at least one, and more typically numerous cytosine residues along at least one of their polynucleotide chains. Consequently, with the crosslinking agent of the present invention, not only is it possible to attach it to a vast number of biologically meaningful polynucleotide carrier chains to which the previously known crosslinking agents could not be attached, but it is also possible in most cases to attach it at multiple attachment sites along such carrier chains. Moreover, since each cytosine residue on the carrier chain becomes paired to a complementary quanine residue on the target chain during base-pairing of the two chains, each molecule of attached crosslinking agent on the carrier chain is assured of an available and accessible crosslinking site on the target chain for its guanine residue-reactive cross-linking moiety. These factors combine to enable a plurality of interstrand crosslinks to be formed between the carrier chain and the target chain, thereby greatly enhancing the probability of effecting an irreversible inactivation of the target chain, regardless of the complexity of its nucleotide sequence or the length of its polynucleotide chain. Hence, the crosslinking agent of the present invention is particularly suitable for use of biological studies involving the information transfer process of replication, repair, recombination, transcription and translation in complex in vitro systems.

Another important feature of the crosslinking agent of the present invention is the fact that the deprotected reactive form of its crosslinking moiety, i.e., the α-haloketone moiety, has a high degree of stability and reaction specificity in biological systems, which provides it with a potentially long life span in such systems without the likelihood of its becoming prematurely deactivated by hydrolysis or side reactions before the carrier chain has been able to become base-paired to its complementary target chain.

DETAILED DESCRIPTION OF PREFERRED EMBODIMENTS

The family of crosslinking agents encompassed by Formula I, above, may be readily synthesized by means of the following synthesis procedure, wherein $n$, $R'$, $X$ and $R$ all have the same meanings as defined above.

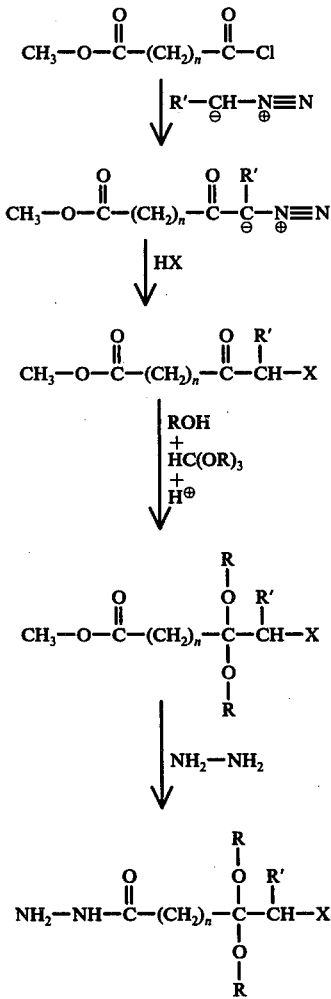

In the above synthesis procedure, the methyl ester-acid chloride starting material of Formula II, i.e., methyl chloroformyl propyrate ($n$ is 2), methyl chloroformyl butyrate ($n$ is 3), or methyl chloroformyl valerate ($n$ is 4) may be obtained commercially or, alternatively, prepared by reacting the corresponding methyl ester-acid with thionyl chloride. The methyl ester-acid chloride starting material of Formula II is first reacted with either diazomethane ($R'$ is hydrogen) or diazoethane ($R'$ is methyl) to form the methyl ester-diazoketone of Formula III, which is then reacted with either HCl or HBr to form the methyl ester-α-haloketone of Formula IV. The compound of Formula IV is then reacted with acid catalysis, with either a mixture of methanol and trimethylorthoformate ($R$ is methyl) or a mixture of ethanol and triethylorthoformate ($R$ is ethyl), to form the methyl ester-α-haloketal of Formula V, which is then reacted with hydrazine to form the final crosslinking agent of Formula I.

An alternative synthesis procedure may be employed for preparing the crosslinking agents of Formula I, when $R'$ is hydrogen, X is Br, and R is methyl. While this alternative synthesis procedure enables large quantities of product to be made quickly and with a minimum of effort, it is less preferred than the synthesis procedure outlined above, since the starting material is more expensive and the final product does not have as high a degree of purity. The starting material of the alternative synthesis procedure is an acid-ketone having the formula

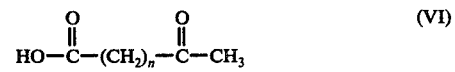

wherein $n$ has the same meaning as defined above. The compound of Formula VI is first reacted with a mixture of bromine, methanol and trimethylorthoformate to form the methyl ester-α-haloketal of Formula V above, wherein $R'$ is hydrogen, X is Br and R is methyl. The methyl ester-α-haloketal is then reacted with hydrazine as in the previously described preferred procedure, to obtain the final crosslinking agent.

The two functional moieties and the linking and spacing chain of methylene groups of the crosslinking agents encompassed by Formula I above, are all properly coordinated with respect to each other so as to provide the crosslinking agent with all of the characteristics necessary for successfully effecting covalent interstrand crosslinks between the paired cytosine residues of polynucleotide carrier chain and guanine residues of a complementary polynucleotide target chain in affinity inactivation procedures. Thus, the acylhydrazide attaching moiety of the crosslinking agent is specifically reactive at the C-4 position of cytosine residues under conditions which are sufficiently mild so as not to be destructive to the polynucleotide carrier chain. Furthermore, when attached to the C-4 position of a cytosine residue, the crosslinking agent will reside in the major groove of a double-helix configuration and hence will not interfere with the base-pairing of the carrier and target chains. Moreover, as explained above, the cytosine residue-reactivity of the acylhydrazide attaching moiety will, in most cases, enable the attachment of a plurality of molecules of crosslinking agent per carrier chain, and also assures that upon base-pairing of the derivatized carrier chain to the complementary target chain, each molecule of crosslinking agent attached to the carrier chain will be brought into proximity with a guanine residue on the target chain, so that multiple interstrand crosslinks can be obtained and irreversible inactivation of the target chain can thereby be effected.

The crosslinking moiety of the crosslinking agent is fully compatible with the acylhydrazide attaching moiety during all stages of the affinity inactivation procedure. In its unreactive protected form, i.e., the α-haloketal moiety, the crosslinking moiety is resistant to hydrolysis under the conditions required for the attachment reaction between the acylhydrazide moiety of the crosslinking agent and the cytosine residues of the polynucleotide carrier chain, and will not react with either the acylhydrazide moiety or the carrier chain, thereby avoiding the possibility of cyclization or polymerization of the crosslinking agent as well as of the formation of intrastrand crosslinks. On the other hand, subsequent to the attachment reaction, the α-haloketal moiety is readily susceptible to hydrolysis to the deprotected reactive form of the crosslinking moiety, i.e., the α-haloketone moiety, under conditions which are sufficiently mild so as not to cause any serious damage to the derivatized carrier chain via depurination. In turn, under the physiological conditions required for base-pairing to proceed, the α-haloketone moiety has a high degree of resistance against hydrolysis and a high degree of reaction specificity toward the N-7 position of a guanine residue, which reduces the likelihood of a premature deactivation of the crosslinking moiety by hydrolysis or side reactions before the derivatized carrier chain has had an opportunity to become base-paired to its complementary target chain. Moreover, since the crosslinking agent is attached to a cytosine residue at its C-4 position which faces the major groove in a double-helix configuration, and since the N-7 position of a base-paired guanine residue likewise faces the major groove, the base-pairing of the derivatized carrier chain to its complementary target chain automatically brings the α-haloketone moiety into proximity with a crosslinking site with which it is specifically reactive, thereby assuring the formation of a covalent interstrand crosslink.

The particular crosslinking moiety of the crosslinking agent of the present invention furthermore offers the flexibility of being able to vary its reactivity by changing the values of either or both of X and R' in Formula I above. Thus, the α-haloketone moiety will have a higher relative reactivity when X is Br than when X is Cl, and also will have a higher relative reactivity when R' is hydrogen than when R' is methyl. While an increase in relative reactivity of the crosslinking moiety will render it more highly reactive with the crosslinking site on the guanine residue of the target chain, there is likely to be a corresponding decrease in its reaction specificity and thus a greater chance for its being prematurely deactivated by side reactions. The flexibility of the crosslinking agent in this regard enables the proper balancing of these characteristics to suit the specific requirements of the particular system in which the crosslinking agent is being employed by proper selection of X and R' in the formula of the crosslinking agent.

The purpose of the chain of methylene groups linking and separating the two functional moieties of the crosslinking agent of Formula I, is to provide the crosslinking agent with the proper molecular length such that when forming a covalent interstrand crosslink between the C-4 position of a cytosine residue on the carrier chain and the N-7 position of a paired guanine residue on the target chain, it will extend substantially the same distance normally separating these two sites of a cytosine-guanine base-pair in a double-helix configuration. This requirement is satisfied when $n$ in Formula I is an integer of from 2 to 4, with the best results generally being obtained when $n$ is 3.

The preferred crosslinking agents in accordance with the present invention for effecting affinity inactivation of nucleic acids, are 6-bromo-5,5-dimethoxyhexanohydrazide (the compound of Formula I wherein $n$ is 3, R' is hydrogen, X is Br and R is methyl); 6-chloro-5,5-dimethoxyhexanohydrazide (the compound of Formula I wherein $n$ is 3, R' is hydrogen, X is Cl and R is methyl); and 6-chloro-5,5-diethoxyhexanohydrazide (the compound of Formula I wherein $n$ is 3, R' is hydrogen, X is Cl and R is ethyl).

The nucleic acid crosslinking agent of Formula I may be employed in affinity inactivation procedures for the selective inactivation of a guanine residue-containing single-stranded polynucleotide target chain having any designated nucleotide sequence. The first step in such procedure is to convert the crosslinking agent into an affinity inactivating agent by attaching it to an appropriate polynucleotide carrier chain. Such carrier chain will be a single-stranded polynucleotide chain having a nucleotide sequence complementary to the designated nucleotide sequence of the target chain and hence capable of base-pairing with the target chain, and, by definition, will contain at least one, and in most instances, a plurality, of cytosine residues having the formula

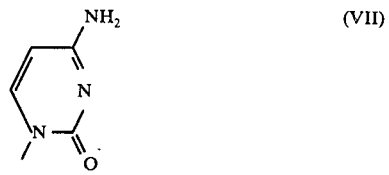

Methods suitable for the preparation of such polynucleotide carrier chains and for the separation of the two strands of double-stranded nucleic acids, are known in the art and do not form a part of the present invention. In this regard, reference is made, for example, to the procedures described by Summers and Szybalski in Biochim. Biophys. Acta, Volume 166, Pages 371–378 (1968), and by Kubinski et al in J. Mol. Biol., Volume 20, Page 313 (1966). In preparing the polynucleotide carrier chain for its derivatization with the crosslinking agent, it is preferable to fragment the carrier chain by sonication to give an average particle weight of $10^5$ daltons. This procedure has the effect of increasing the number of reactive particles per unit mass of the final inactivating agent and should not affect its inactivating capabilities since covalent crosslinks along any significant portion of the target chain should result in its inactivation.

The attachment of the crosslinking agent to the polynucleotide carrier chain is effected by reacting these two components in an acidic aqueous reaction medium having a pH and water concentration such that both reactants are soluble in the reaction medium and the α-haloketal moiety of the crosslinking agent is not hydrolyzed. While a certain minimum water concentration is required in order to maintain solubility of the carrier chain, and while a certain maximum pH is required in order for the attachment reaction to proceed at a reasonable rate, too high a water concentration or too low a pH increases the hydrolysis rate of the α-haloketal moiety to an unacceptable level. Consequently, the attachment reaction should be carried out at a minimum water concentration compatible with the solubility of the carrier chain and at a maximum pH compatible with a reasonable attachment rate. A reaction medium found to be particularly suitable is one comprising water and an alcohol selected from the group consisting of methanol and ethanol in a water to alcohol volume ratio of from 2:3 to 3:2, preferably about 1:1, and having a pH within the range of from 3.3 to 4.8, preferably about 4.1. The attachment reaction proceeds under these conditions at room temperature and at a reasonable rate.

During the attachment reaction, the acylhydrazide attaching moiety of the crosslinking agent reacts specifically at the C-4 position of a cytosine residue on the carrier chain, i.e., displacing the free $NH_2$ group of the cytosine residue of Formula VII, to thereby covalently link a molecule of the crosslinking agent to the cytosine residue and convert the latter to a C-4 substituted cytosine residue having the formula

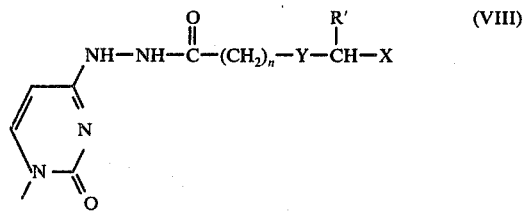

wherein y is

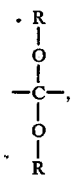

and $n$, $R'$, $X$ and $R$ have the same meanings as defined above. Since in most cases the carrier chain being derivatized will contain numerous cytosine residues along its length, the resulting derivatized carrier chain will generally contain a plurality of the C-4 substituted cytosine residues of Formula VIII. At this stage of the procedure, the derivatized carrier chain constitutes the affinity inactivating agent of the present invention in its as yet unactivated form, i.e., wherein the crosslinking moiety of each attached molecule of crosslinking agent is still in its unreactive protected form as an α-haloketal moiety.

The next step in the procedure is to activate the derivatized carrier chain by hydrolyzing the α-haloketal moiety of each attached molecule of crosslinking agent to the guanine residue-reactive α-haloketone moiety. While such hydrolysis requires acidic conditions below a certain maximum pH, the acidic conditions must be sufficiently mild so as not to cause the derivatized carrier chain to precipitate or to be seriously damaged via depurination reactions. Thus, the activation step should be carried out in an acidic aqueous activation medium having a pH at which the derivatized carrier chain is soluble, the α-haloketal moiety is hydrolyzable at a reasonable rate, and the derivatized carrier chain is otherwise stable. A pH within the range of from 2.5 to 3.5, preferably about 2.5, is generally suitable for this purpose. Under these conditions, hydrolysis of the α-haloketal moiety proceeds at a reasonable rate at room temperature. The presence in the activation medium of a trace of salt, sufficient to provide the activation medium with an ionic strength equivalent to up to about 0.9 M NaCl, both enhances the hydrolysis rate of the α-haloketal moiety and inhibits depurination of the carrier chain. This effect can be achieved by employing a buffer salt (e.g., chloroacetic acid-NaOH) for adjusting the pH of the activation medium to within the required range.

The effect of the activation step is to convert Y in the C-4 substituted cytosine residues of Formula VIII to the

group. The resulting activated derivatized carrier chain constitutes the affinity inactivating agent of the present invention in its activated form, i.e., wherein the crosslinking moiety of each attached molecule of crosslinking agent is in its deprotected reactive form as an α-haloketone moiety.

The final step in the affinity inactivation procedure is to contact the activated derivatized carrier chain with its complementary target chain under substantially physiological conditions, i.e., at about 37° C. employing an aqueous contacting medium having a pH within the range of from 5.0 to 9.0, preferably about 7. The contacting medium preferably contains a denaturing agent, such as dimethyl sulfoxide, formamide or sodium perchlorate. Under such conditions, the activated derivatized carrier chain will complex with its complementary target chain into a hydrogen-bonded base-paired double-stranded configuration wherein each C-4 substituted cytosine residue of the carrier chain is paired with a complementary guanine residue of the target chain in the manner indicated by Formula IX below.

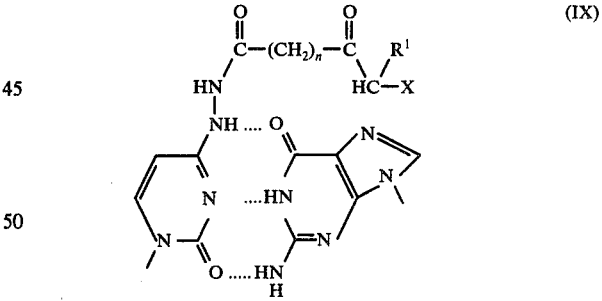

As can be seen from Formula IX, the base-paired configuration of the two complementary chains brings the α-haloketone moiety of each C-4-substituted cytosine residue of the carrier chain into accessible proximity with the N-7 position of its respective base-paired guanine residue of the target chain. Since the α-haloketone moiety has a high degree of reaction specificity toward the N-7 position of a guanine residue, it will react with the guanine residue at such site to form an interstrand covalent crosslink between the cytosine-guanine base-pair, as indicated in Formula X below.

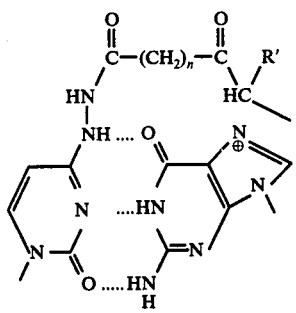

The affinity inactivating agents of the present invention will generally contain a relatively high density of the C-4 substituted cytosine residues per unit length of the carrier chain, and thus will result in a correspondingly high density of interstrand crosslinks formed in the above manner between the carrier chain and the target chain. Such high density of crosslinks will not be readily subject to repair mechanisms and hence will maintain the target chain stably complexed together with the carrier chain in the double-stranded configuration, thereby effecting an irreversible inactivation of the target chain.

In the above-described affinity inactivation procedure, the affinity inactivating agent of the present invention will not crosslink with any nucleotide sequence which is non-complementary to that of the polynucleotide carrier chain, and hence is highly specific to the complementary polynucleotide target chain. Such high specificity enables the utility of the materials and procedures of the present invention in a wide variety of possible applications involving complex biological systems which contain numerous extraneous materials.

In vitro applications of the materials and procedures of the present invention include their use as a biochemical research tool for selectively inactivating or blocking specific nucleotide sequences as a means of determining their function, and for elucidating the mechanisms underlying the information transfer processes of replication, transcription and translation.

The invention is further illustrated by way of the following examples.

EXAMPLE 1

The synthesis of 6-bromo-5,5-dimethoxyhexanohydrazide was carried out in the following manner.

A 0.06 mole sample of methyl chloroformyl butyrate (Aldrich Chem. Co.) was added with stirring to an excess of diazomethane in ether at room temperature. After 2 hr gaseous HBr was bubbled through the solution until the yellow color of the diazoketone was dissipated. The solution was neutralized with sodium bicarbonate, washed three times with water, concentrated at reduced pressure, and finally distilled (bp. 111° C./0.05mm) to give 12 g of the bromoketone. The product was contaminated with approximately 8% of the chloroketone (produced as a side product in the formation of the diazoketone).

A mixture of 0.05 mole of the bromoketone, 20 ml of trimethylorthoformate, 30 ml methanol, and 0.1 g p-toluenesulfonic acid was kept at 50° C. overnight. The solution was neutralized with 10 ml saturated ammonium carbonate, concentrated at reduced pressure, and partitioned between ether and water. After washing the organic phase twice with water the ether was removed at reduced pressure and the residue was mixed with two equivalents of hydrazine plus sufficient methanol to give a homogeneous solution. After 18 hrs at 37° C. the mixture was concentrated in vacuo and triturated twice with ether leaving an insoluble residue which was discarded.

The ether solution was dried to give the crude product. This material was crystallized by dissolving in warm benzene, adding pentane to incipient cloudiness and cooling slowly to 5° C. after crystallization began. By this procedure a 50% yield of 6-bromo-5,5-dimethoxyhexanohydrazide (contaminated with 8% of the chloro analog) was obtained, mp. 58°-60° C. Spectral analysis gave the following, ir(CHCl$_3$) cm$^{-1}$:3350, 3470, 3640 (C—H); 1670, 1630 (C=O); nmr (CDCl$_3$) ppm: 1.7 (m,4H), 2.1 (t,2H), 3.2 (s,6H), 3.8 (br,2H), 7.4 (br,1H). The bromomethyl resonance occurred as a singlet at 3.4 ppm while the corresponding peak of the contaminating chloro analog occurred at 3.5 ppm. Elemental analysis: calculated for C$_8$H$_{17}$BrN$_2$O$_3$ (269.15); contaminated with 8% of the chloro analog: C: 36.26; H: 6.47; Br: 28.57; N: 10.57, found: C: 36.27; H: 6.50; Br: 28.59; N: 10.54. The mass spectrum showed no parent peak but did show doublets indicating loss of fragments of mw 31 and 63.

EXAMPLE 2

The synthesis procedure of Example 1 was repeated, but this time employing HCl in place of the HBr. The resulting product was 6-chloro-5,5-dimethoxyhexanohydrazide.

EXAMPLE 3

The synthesis procedure of Example 2 was repeated, but this time replacing the mixture of trimethylorthoformate and methanol with a corresponding mixture of triethylorthoformate and ethanol. The resulting product was 6-chloro-5,5-diethoxyhexanohydrazide.

EXAMPLE 4

The 6-bromo-5,5-dimethoxyhexanohydrazide synthesized in accordance with Example 1, was employed for linking cytidine to guanosine by the following procedure.

A methanol/water (1:1 by vol) solution was saturated with cytidine (A$_{271}$=2940) and 0.1 ml added to 0.11 g 6-bromo-5,5-dimethoxyhexanohydrazide. The mixture was adjusted to pH 4.1 with 1 μl formic acid (91%) and incubated 6 hr at 37° C. Five ml of ether was added and the preparation filtered. The residue was fractionated by descending paper chromatography (Whatmann 3MM developed with solvent A, n-butanol/water/ethanol (16/5/2 by vol). The cytidine adduct (R$_f$0.58), viewed under 254 nm light, was eluted with water and rechromatographed with solvent B, isopropanol/1% aqueous ammonium formate (2/1 by vol). With this solvent the product moved with an R$_f$ of 0.79. After elution with water and drying the product was resuspended in 0.09 ml water to give a solution of A$_{275}$=10,000. One μl formic acid (91%) was added to give pH 2.5 and the preparation incubated overnight at 25° C. One half ml of formamide saturated with guanosine (A$_{252}$=5040) was added and the preparation incubated at 37° C. for 5 days. The reaction mixture was subjected to paper electrophoresis using 0.05 M ammonium acetate buffer adjusted to pH 5.5 with acetic acid. The reaction product, which showed a deep blue fluorescence under 254 nm light, moved with an electrophoretic mobility of +1(relative to picric acid as −1). The product was eluted and further purified by descending paper chromatography developed with solvent B. The high electrophoretic mobility fraction chromatographed as a single component with an $R_f$ of 0.35. The product yield was estimated to be 25% based on the $A_{300}$ at pH 13.

The resulting product had spectral properties at pH 1,5.5 and 13 expected for a compound containing both 4-deamino-4-acylhydrazidocytidine and 7-acetonylguanosine, indicating a covalent linkage of an acylhydrazide moiety at the C-4 position of cytosine and a covalent linkage of a ketone moiety at the N-7 position of guanine.

EXAMPLE 5

This example illustrates the interstrand crosslinking of T7 bacteriophage DNA by the affinity inactivation procedure of the present invention, employing the 6-bromo-5,5-dimethoxyhexanohydrazide crosslinking agent synthesized in accordance with Example 1.

The procedures for preparation and strand separation of T7-DNA were adapted from Summers and Szybalski, Biochim. Biophys. Acta, Vol. 166, pages 371–378 (1968). One half mC of radioisotopically labeled DNA precursor ($H_3{}^{32}PO_4$ or $^3H$-thymidine) was added to 70 ml containing 0.56 g bactotryptone and 0.28 g NaCl. After autoclaving 0.7 ml 50% (wt/vol) sterile glucose was added, the medium was inoculated with E. coli B and incubated overnight at 25° C. with bubbling. The labeled culture was poured into 1.5 l of the same medium (unlabeled) and incubated at 37° C. with bubbling. At an $A_{550}$ of 0.6, $7.5 \times 10^{10}$ T7 phage were added and incubation continued. After 40 minutes 35 g NaCl was added. After dissolution 270 ml of 30% polyethylene glycol 6000 and 30 ml 10% dextran sulfate 500 were added and the lysate stored 18 hr at 4° C. The top phase was discarded and the interphase and lower phase centrifuged 10 min at 10,000 g, 4° C. The interphase cake was resuspended in 6 ml water and 0.9 ml 3 M KCl added. After centrifugation for 10 min at 10,000 g, 4° C., the supernatant was decanted; its density was adjusted to 1.5 with CsCl; and it was banded by centrifugation for 18 hr in a Beckman 50Ti anglehead rotor, 35,000 rpm, 4° C. The T7 band was removed and dialyzed against 1 mM EDTA pH 7.5.

The T7 preparation was diluted to give an $A_{260}$ of 30 at pH 13. Phage suspension (2.8 ml), 0.7 ml polyG solution (3.2 mg/ml in 1 mM EDTA pH 7.5), 7 μl 30% aqueous sarkosyl, and 7 μl M NaOH were mixed and heated 3 min in a boiling water bath; quenched in an ice bath; and 0.7 ml tris buffer (0.5 M Trizma base to pH 7.5 with HCl) added. The density was adjusted to 1.76 g/ml by adding about 18 ml saturated CsCl solution. The preparation was centrifuged 72 hr in thickwalled polycarbonate bottles in a Beckman 50.2Ti anglehead rotor at 32,000 rpm, 10° C. Half ml fractions were collected and assayed for radioisotope. Fractions were combined to give two preparations, one containing light strand and the other containing heavy strand complexed with polyG. Each preparation was adjusted to 0.1 M NaOH, incubated 16 hr at 37° C.; adjusted to pH 5 with acetic acid; and precipitated at 4° C. with 2 vol ethanol. After centrifugation for 5 min at 5000 g, 4° C., the co-precipitating CsCl was removed by washing three times with 20 ml volumes of ethanol/0.05 M ammonium acetate (7/3 by vol). The $^{32}P$ labeled heavy strand was fragmented by resuspending in 0.01 M NaOH at a concentration of $A_{260} = 15$ and sonicating 30 seconds.

To 0.6 ml of the fragmented DNA solution, 0.75 g 6-bromo-5,5-dimthoxyhexanohydrazide, 0.6 ml methanol, and 36 μl formic acid (91%) were added to give a final pH of 4.1. After a 2 hr incubation at 37° C., 8 ml ethanol was added; the preparation was chilled 2 hr at 0° C., centrifuged 10 min at 10,000 g, 4° C., and the supernatant discarded. The precipitate was washed with ethanol and dried.

The resulting derivatized heavy fragments were suspended in $10^{-3}$ M NaOH at a concentration of $A_{260} = 10$ and one half ml was activated by adjusting to pH 2.5 with 0.1 ml chloroacetate buffer (0.6 M chloroacetic acid to pH 2.5 with NaOH). After 90 minutes at 25° C., 0.4 ml of the activated fragments was withdrawn and neutralized with sodium citrate buffer (1 vol 5 M NaOH, 1 vol 1.5 M citric acid).

Both light and heavy strand preparations labeled with $^3H$-thymidine were suspended in formamide at a concentration of $A_{260} = 15$. Half of the neutralized activated derivatized fragment preparation was mixed with an equal volume of formamide solution containing light (complementary) strand DNA (preparation A). The remaining activated derivatized fragment preparation was mixed with an equal volume of formamide solution containing heavy (noncomplementary) strand DNA (preparation B). Both tubes were capped and incubated for 18 hr at 37° C.

Following incubation, the preparations A and B were each mixed with 2 volumes of 0.15 M NaOH and layered over an alkaline (0.1 M NaOH throughout) sucrose (10% to 25% with 1 ml 40% cushion) gradient. The gradients were centrifuged 14 hr at 40,000 rpm, 10° C., in a Beckman 41Ti swinging bucket rotor. Half ml fractions were collected and assayed for $^3H$ and $^{32}P$.

The distribution of $^3H$ and $^{32}P$ following fractionation of preparation A on the alkaline gradient indicated the cosedimentation of the activated derivatized fragments with their complementary strands. This demonstrates the presence of interstrand covalent crosslinks between the complementary sequences, since such linkages are necessary for cosedimentation of the strands and fragments to occur under conditions which denature DNA. On the other hand, the distribution of $^3H$ and $^{32}P$ following fractionation of preparation B on the alkaline gradient indicated differing sedimentation rates of the activated derivatized fragments and their noncomplementary strands. This demonstrates a lack of interstrand covalent crosslinking between the noncomplementary sequences. From the above results, it can be concluded that the crosslinking agent of the present invention will covalently link a derivatized polynucleotide only to a complementary nucleotide sequence and not to noncomplementary nucleotide sequences.

The Embodiments of the Invention in which an Exclusive Property or Privilege is claimed are defined as follows:

1. A crosslinking agent for covalently crosslinking the base-paired complementary polynucleotide chains of a double-stranded nucleic acid having cytosine and guanine residues, said crosslinking agent having the formula

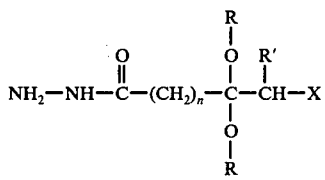

wherein $n$ is an integer of from 2 to 4; R' is hydrogen or methyl; X is Cl or Br; and R is methyl or ethyl.

2. The crosslinking agent of claim 1, which is 6-bromo-5,5-dimethoxyhexanohydrazide.

3. The crosslinking agent of claim 1, which is 6-chloro-5,5-dimethoxyhexanohydrazide.

4. The crosslinking agent of claim 1, which is 6-chloro-5,5-diethoxyhexanohydrazide.

5. An affinity inactivating agent for nucleic acids which is adapted for use in selectively inactivating a guanine residue-containing single-stranded polynucleotide target chain having a designated nucleotide sequence by base-pairing and covalently crosslinking therewith, said affinity inactivating agent comprising a derivatized cytosine residue-containing single-stranded polynucleotide carrier chain which has a nucleotide sequence complementary to said designated nucleotide sequence and which is capable of base-pairing with said target chain, at least one of the cytosine residues of said derivatized carrier chain being a C-4-substituted cytosine residue having the formula

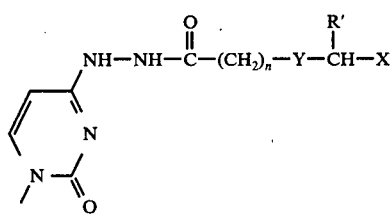

wherein $n$ is an integer of from 2 to 4; R' is hydrogen or methyl; X is Cl or Br; Y is

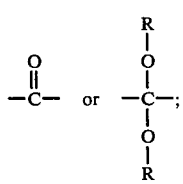

when Y is

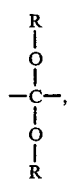

R is methyl or ethyl.

6. The affinity inactivating agent of claim 5, wherein said derivatized carrier chain contains a plurality of said C-4-substituted cytosine residues.

7. The affinity inactivating agent of claim 5, wherein X is Br, $n$ is 3, R' is hydrogen and R is methyl.

8. A method for the selective inactivation of a guanine residue-containing single-stranded polynucleotide target chain having a designated nucleotide sequence, comprising the steps of:

(a) providing a cytosine residue-containing single-stranded polynucleotide carrier chain which has a nucleotide sequence complementary to said designated nucleotide sequence and which is capable of base-pairing with said target chain;

(b) reacting said carrier chain with a crosslinking agent having the formula

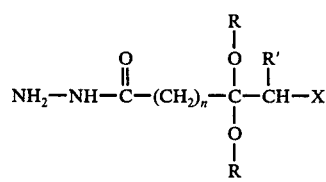

wherein $n$ is an integer of from 2 to 4; R' is hydrogen or methyl; X is Cl or Br; and R is methyl or ethyl; so as to form a derivatized carrier chain wherein at least one of the cytosine residues of said carrier chain is covalently linked to the acylhydrazide moiety of a molecule of said crosslinking agent and thereby converted to a C-4-substituted cytosine residue having the formula

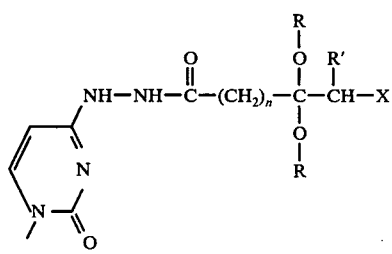

wherein $n$, R', X and R have the meanings defined above;

(c) activating said derivatized carrier chain by hydrolyzing the

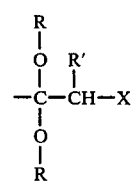

moiety of said C-4-substituted cytosine residues to a guanine residue-reactive

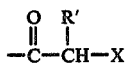

moiety wherein R' and X have the meanings defined above; and (d) contacting said activated derivatized carrier chain with said target chain under substantially physiological conditions, whereby said carrier chain and said target chain become base-paired and said C-4-substituted cytosine residues of said carrier chain react through said guanine residue-reactive moiety with their respective base-paired guanine residues of said target chain to covalently crosslink the two chains and thereby inactivate said target chain.

9. The method of claim 8, wherein the reaction of said carrier chain with said cross-linking agent is carried out in a reaction medium comprising water and an alcohol selected from the group consisting of methanol and ethanol in a water to alcohol volume ratio of from 2:3 to 3:2, and the pH of said reaction medium is within the range of from 3.3 to 4.8.

10. The method of claim 8, wherein the activation of said derivatized carrier chain is carried out in an acidic aqueous activation medium having a pH within the range of from 2.5 to 3.5.

11. The method of claim 8, wherein said derivatized carrier chain contains a plurality of said C-4-substituted cytosine residues.

12. The method of claim 8, wherein said crosslinking agent is 6-bromo-5,5-dimethoxyhexanohydrazide.

* * * * *